United States Patent [19]

Greenwald et al.

[11] 4,106,128

[45] Aug. 15, 1978

[54] ENDOPROSTHETIC BONE JOINT

[76] Inventors: A. Seth Greenwald, 2235 Tudor Dr., Cleveland Heights, Ohio 44106; Derek S. Porritt, 3263 Granger Rd., Medina, Ohio 44256; Mary-Blair Matejczyk, 3617 Randolph Rd., Cleveland Heights, Ohio 44121

[21] Appl. No.: 747,502

[22] Filed: Dec. 6, 1976

[51] Int. Cl.² ............................................. A61F 1/24
[52] U.S. Cl. .................................. 3/1.91; 128/92 C
[58] Field of Search ..................... 3/1.91, 1.911, 1.912, 3/1; 128/92 C

[56] References Cited

U.S. PATENT DOCUMENTS

| 3,506,982 | 4/1970 | Steffee ................................... 3/1.91 |
| 3,795,922 | 3/1974 | Herbert et al. ................. 128/92 C X |
| 3,837,008 | 9/1974 | Bahler et al. ......................... 3/1.91 |
| 3,868,730 | 3/1975 | Kaufer et al. ......................... 3/1.91 |
| 4,003,096 | 1/1977 | Frey ....................................... 3/1.91 |

FOREIGN PATENT DOCUMENTS

| 2,309,432 | 11/1973 | Fed. Rep. of Germany ............. 3/1.91 |
| 1,362,187 | 7/1974 | United Kingdom ...................... 3/1.91 |
| 1,333,412 | 10/1973 | United Kingdom ..................... 3/1.911 |

Primary Examiner—Ronald L. Frinks
Attorney, Agent, or Firm—Fay & Sharpe

[57] ABSTRACT

A prosthetic joint of the type used to replace dysfunctional non-weight bearing joints such as the knuckle, wrist, elbow or shoulder. The preferred embodiment comprises a radial component connected by a concavo-convex socket component to a metacarpal component. The radial component has an intramedullary stem terminating in a cup having a plurality of inwardly extending pins. The concavo-convex socket component is retained in the cup by the articulation of the pins with a plurality of flats which communicate with slots which terminate in apertures. The concavo-convex component includes an opening extending inwardly from one end thereof which defines two communicating bearing surfaces, with the innermost surface being spherical and the outer surface being frusto-conical and having an elliptical cross-section. The metacarpal component includes a ball, a neck area and an intramedullary stem. The ball articulates with the spherical surface of the concavo-convex member component and the neck, which also has an elliptical cross-section, articulates with the frusto-conical surface. The intramedullary stem which is connected to the cup is offset volarly by an amount equal to the offset in the metacarpal component thereby providing a greater moment arm for the weaker tendons of the wrist.

4 Claims, 9 Drawing Figures

ENDOPROSTHETIC BONE JOINT

BACKGROUND OF THE INVENTION

This invention relates to surgically implantable prosthetic devices and more particularly such devices for the replacement of non-weight bearing joints.

While the invention finds particular use as a replacement for a dysfunctional wrist joint and will be described in the context, it will be appreciated by those skilled in the art that the invention has broader applications and is applicable to other joints. Such joints include, for example, the metacarpophalangeal, thumb carpometarcarpal, radiohumeral and glenohumeral articulations.

Currently, there are devices available for either total or partial replacement of the knuckle, wrist, elbow, shoulder, hip, knee and ankle joints. These devices use one or more of the possible types of mechanical articulations available; that is, hinge, ball and socket, or runners in grooves. Most devices use intramedullary stems and acrylic bone cement to secure the prosthesis to bone. Presently available prostheses have components constructed from several types of biologically inactive metals and designed to articulate with other components constructed from a plastic, such as high density polyethylene.

Several methods or techniques are used to insure that the components remain articulated, and these methods include the use of the soft tissues existent at the time of implantation, the use of pins or screws to hold articular surfaces together and the use of bayonet type locks. Some types of the available prostheses are quite simple while other types comprise complex mechanical systems, with both types having attendant or inherent disadvantages. The principal disadvantage of the simple prosthesis is that they may not reproduce the full range of motion of the joint. The principal disadvantage of the complex prosthesis is due to the potential complexities of surgery and increased chance of failure. Typical causes of such failure include fracture of bone during reaming and breakage of the implant itself. Additionally, the prosthesis components, such as pins, screws or intramedullary stems work loose following implantation. In the event of failure, fusion may be required, but such surgery may be difficult if a great deal of bone has been removed.

PRIOR ART DEVELOPMENTS

In the prior art there are four known developments in wrists, two of which have been patented and two of which are found in the literature. Each will be evaluated by examining these three criteria:

a. Ease of surgery: How much bone needs to be removed in order to implant the prosthesis.

b. Articulation: How do the components remain articulated.

c. Center of rotation: Is the center of rotation of the prosthesis in line with the longitudinal axis of the prosthesis.

Brief comments concerning the developments follow:

MUELI — "Prothese Totale du Poignet" — Protek SA, Berne, Switzerland a. The Mueli components have two prongs. The metacarpal component is implanted in the second and third metacarpals. The navicular, the lunate and the capitate must be removed in order to implant the metacarpal component.

b. Articulation is maintained solely by the existent soft tissue. If such tissue is deformed, the prosthesis cannot aid in correcting the deformity.

c. The axes are co-linear.

VOLZ — 116 Clinical Orthopaedics and Related Res., 209–14 a. The Volz concept also has a two-pronged metacarpal component. The navicular, the lunate and one-half the capitate must be removed. Part of the triquetrum may also be removed to facilitate radial-ulnar deviation. Channels are drilled into the second and third metacarpals.

b. The motion is performed by a cylinder which articulates with a surface which surrounds it. The articular surface pinches the cylinder, but is held in articulation by the existent soft tissue.

c. The center or rotation is offset slightly in the radial direction.

BAHLER, et al. — U.S. Pat. No. 3,837,008 a. The patent does not provide details of the surgery. There is only one metacarpal stem. Judging from the size of the socket, at least the lunate and part of the capitate must be removed. Possibly part of the navicular or the triquetrum may be removed.

b. The ball is held in the socket by a self-tapping screw which keeps the halves of the socket together.

c. The compounds are co-linear.

LENNOX — U.S. Pat. No. 3,909,853 a. All the carpals except for the trapezium and part of the navicular must be removed. Four metacarpals must be reamed.

b. The metacarpal stems are held in the carpal component by self-tapping screws. The radial component is held in a socket on the carpal component by means of flats on the ball which allow it to fit into the socket.

c. The radial ball and carpal socket are transversely offset.

In like manner, the following evaluation is made of the present invention:

a. The lunate, one-half of the capitate and possibly part of the navicular must be removed. Only the third metacarpal is reamed.

b. The ball is encapsulated in the socket and has a pullout strength of 113 ± 3 pounds. The socket is held within the radial cup.

c. The center of rotation has a volar offset from the longitudinal axis of the stem.

OPTIMAL CONDITIONS FOR EACH CRITERIA a. Surgery should be simple. The less bone removed, the easier the surgery. The present invention and Bahler U.S. Pat. No. 3,837,008 require simple surgery by reason of single stem design.

b. Articulation should not depend on the existent soft tissue. Clinical experience shows that such reliance gives poor results as far as regaining motion is concerned. Self-tapping screws can work loose or corrode. In either case, adverse effects are likely.

c. In the present invention the volar offset provides a large moment arm for the extensor tendors. Such mechanical advantage is essential for extension. Transverse offsets do not provide a moment arm for these tendons.

The present invention overcomes the above referred to problems and disadvantages encountered with prior prostheses and provides a new prosthetic joint which has the following characteristics:

1. Possibility of fusion. In case of failure, enough bone remains for fusion.

2. Range of motion. In both dorsiflexion and palmar flexion, an average normal wrist has maximal motion of 85° from neutral anatomical position. However, useful motion in these directions is less than full flexion, and most useful motion occurs within 40° of neutral position. The present invention allows for such motion. In ulnar and radial deviation, the maximum range of motion is approximately 55° ulnar and 15° radial deviation. But, as with flexion, the useful range of motion is less than the full range. The present invention has a range of 25° in both directions, which approximates the useful range. Circumduction is possible within the cone described and closely approximates the useful range of motion.

3. Articulation surface. In the present invention there is no metal to metal contact. The lack of such contact is beneficial to the friction and wear characteristics of the device. Persons skilled in the art know that the absence of metal to metal contact is beneficial in avoiding failure after implantation.

4. Versatility. It is an object of this invention to be readily adaptable to joints with structures similar to the wrist. By modifying the frusto-conical bearing surface of the concavo-convex component (see description below), the range of motion can be changed to match the motion of other joints.

The present invention meets all of these objects and generally provides an endoprosthetic joint device comprising a radial component connected by a concavo-convex component to a metacarpal component. The radial component has an intramedullary stem which terminates in a cup which contains a plurality of pins. Held within the cup is the concavo-convex component which is secured therein by the articulation between the pins and a plurality of diametrically placed flats, each of which communicates with slots which terminate in apertures. The concavo-convex component contains a plurality of communicating bearing surfaces, one of which is spherical, the other of which is frusto-conical with an elliptical cross-section. The metacarpal component has a spherical ball which is encapsulated by the spherical bearing surface. The ball is integrally attached to a neck with an elliptical cross-section. The neck is free to move within the volume defined by the frusto-conical surface. The neck is integrally attached to a step which connects the neck to an intramedullary stem, which is used to fix the metacarpal component to the metacarpal bone. The center lines of the radial and metacarpal intradedullary stems are colinear when the prosthesis is in neutral anatomical position. The center of rotation of the ball in the spherical surface is offset in the volar direction from the longitudinal axis defined by the center lines of the stems.

In The Drawings:

For a fuller understanding of this invention, the same will now be described by way of exanmple with reference to the accompanying drawings in which.

DESCRIPTION OF THE INVENTION

Figure 6:
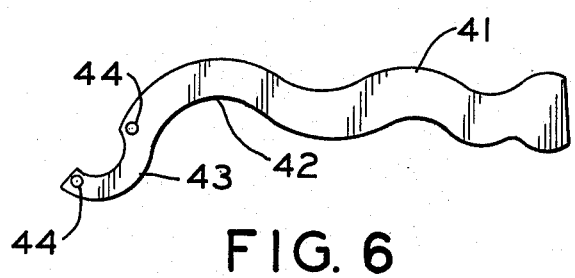
FIG. 6 is a plan view of the wrench used to articulate the components.

The illustrated device comprises a radial component 10, a concavo-convex socket component 20, a metacarpal component 30 (FIG. 1), and a wrench (FIG. 6).

The radial component 10 comprises a radial intramedullary stem 11 integral with a radial cup 13. The radial component is designed to be implanted by reaming an intramedullary channel into the radius bone of the forearm. The stem is substantially circular in cross-section and tapers toward its proximal end. This stem 11 has a flat surface 12, which is used as a guide for insertion of the stem 11 into the radius bone. The flat surface or guide 12 defines the posterior surface of the stem and extends the entire length of the stem. The cup 13 is U-shaped in exterior cross-section. The exterior diameter of the proximal plane of the cup 13 is greater than the diameter of the stem 11. The interior surface 14 of the cup 13 is generally concave. Cup 13 contains two apertures 15, diametrically positioned. Two cylindrical pins 16 are welded into these apertures and extend into the interior surface 14. The outside of the cup 13 has a groove or indicia 17 which is coextensive with the center line of the flat surface or guide 12. These latter features establish the longitudinal axis of the radial stem. The longitudinal axis of the cup 13 is offset from the longitudinal axis of the stem 11, as may be seen in connection with FIG. 1A. The offset is in the volar direction. The function of the offset will be described in connection with the mechanical properties of this device, as presented below.

Figure 1:
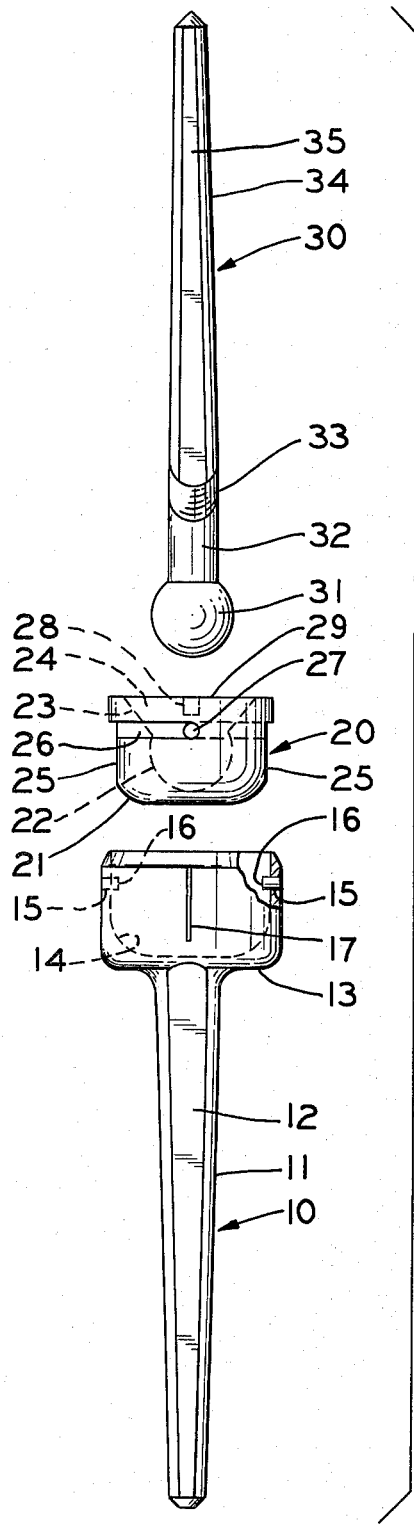
FIG. 1 is a prosthetic wrist joint device in an exploded plan view of the neutral anatomical position at the posterior surface.
Figure 1A:
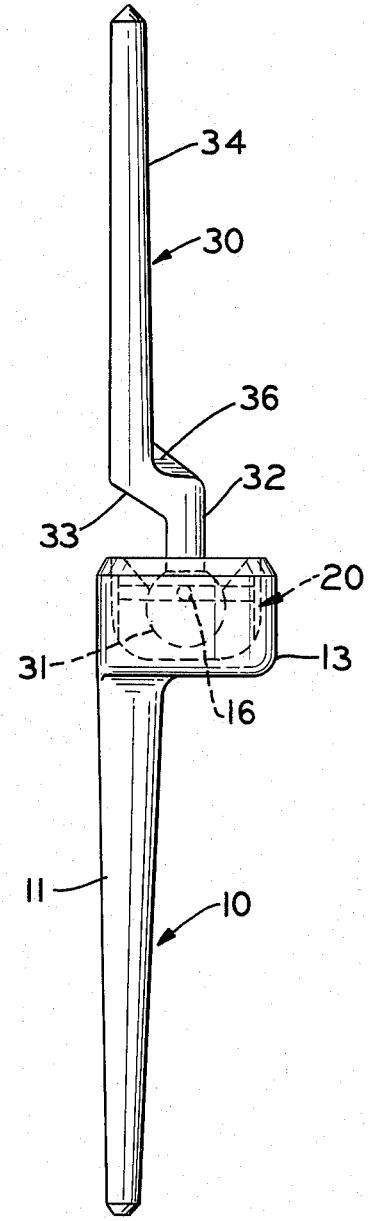
FIG. 1A is a side view of the prosthesis showing the volar offset of the center of rotation.
Figure 2:
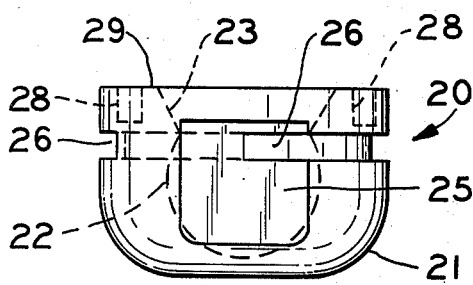
FIG. 2 is a side view of the socket component.
Figure 3:
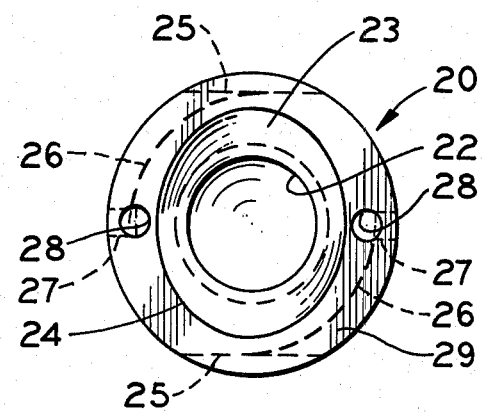
FIG. 3 is a top view of the socket component showing the frontal plane and elliptical orifice.
Figure 4:
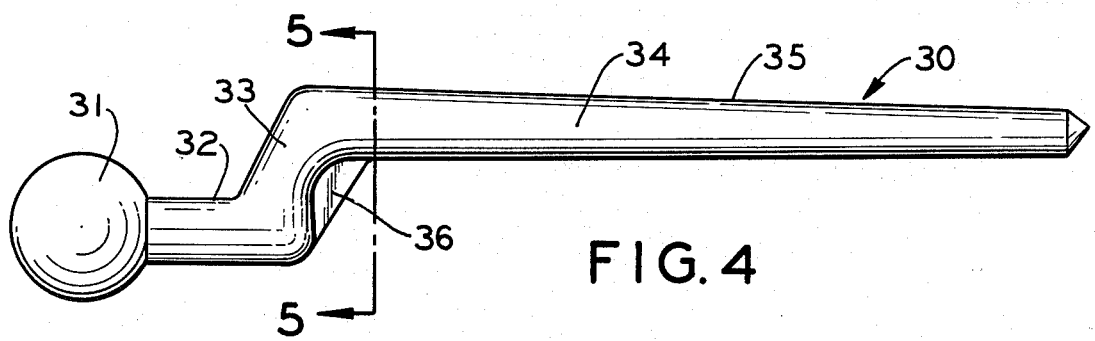
FIG. 4 is a side view of the metacarpal component.
Figure 5:
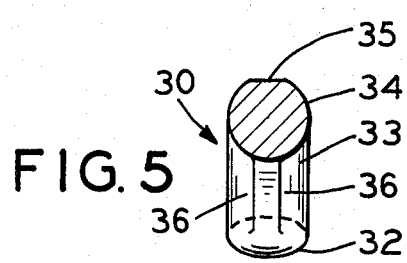
FIG. 5 is a cross-sectional view of the neck and step of the metacarpal component.

FIGS. 1, 2 and 3 illustrate the concavo-convex socket component 20 which has a number of bearing surfaces, one of which is concave or spherical 22, the other of which is frustoconical 23 with an elliptical cross-section as seen in FIG. 3. The spherical surface 22 subtends a solid angle greater than $2\pi$ steradians. If the frusto-conical surface 23 were extended to its apex, such apex would be within the sphere. This concavo-convex component 20 has an outer convex surface 21, which mates with the concave surface 14 of cup 13. The concavo-convex geometry of this component is established. The concavo-convex component also contains a bayonet slot 26 to guide the pins 16 into apertures 27 to lock the concavo-convex component within the cup 13. On opposite sides of the concavo-convex component 20 are complementary slots and apertures to provide secure fastening of the socket component in the cup 13. The depth of the slots 26 are not uniform but decrease by 0.008 inch as they run from an outer surface 25 to the apertures 27. The function of these slots will be fully described in connection with the locking means.

In the frontal plane 29 of the socket is an elliptical orifice 24 formed by the intersection of the frusto-conical surface 23 with the frontal plane 29. Outwardly of the semiminor axis of the orifice 24 are the locking apertures 28.

The metacarpal component 30 comprises a spherical ball 31 having a neck 32 with an elliptical cross-section, a step 33 and an intramedullary stem 34. The metacarpal intramedullary stem is similar to the radial stem 11 in that both taper (toward the distal end in the metacarpal component), have a generally circular cross-section, and have a flat guide surface such as surface 35 on the metacarpal component, which runs the length of the stem and defines the posterior surface of the stem. When the prosthesis is in an anatomically neutral position, the longitudinal axis of the metacarpal stem 34 is coextensive with the longitudinal axis of the radial stem 11. The diameter of the ball 31 is greater than the neck 32. The distal surface of the step 33 may be notched at 36 to collect any excess bone cement displaced during implantation.

The wrench (FIG. 6) has a handle 41, a connector 42, a head 43 and a pair of cylindrical locking studs 44. The head 43 is placed at an angle to the handle, the measure of which is fixed by the connector.

The preferred materials for the radial and metacarpal components are biologically inactive metals. The socket component should be of a suitably compatible plastic material such as high density polyethylene.

Prior to implantation, the concavo-convex component 20 and the metacarpal component 30 are assembled by heating the plastic concavo-convex component. The ball 31 is encapsulated within the spherical bearing surface 22. The encapsulation is load supporting because the spherical surface subtends a solid angle greater than $2\pi$ steradians. Though encapsulated the ball 31 is free to rotate. Once these components are assembled the device is ready for implantation.

Figure 7:
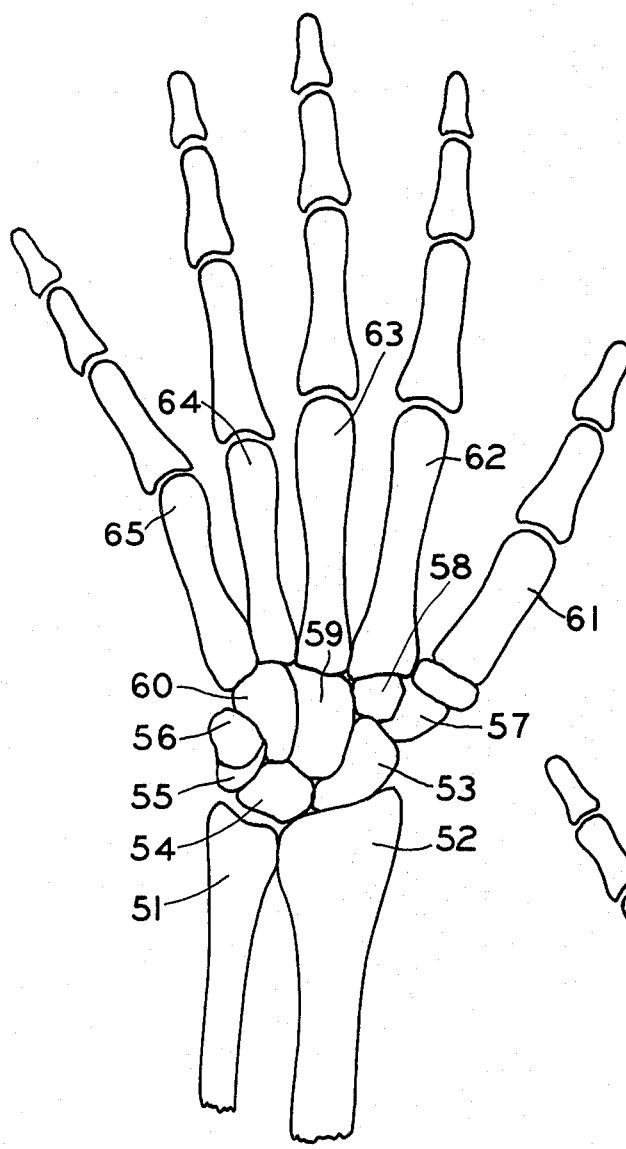
FIG. 7 shows the anatomical bones of a normal hand.
Figure 8:
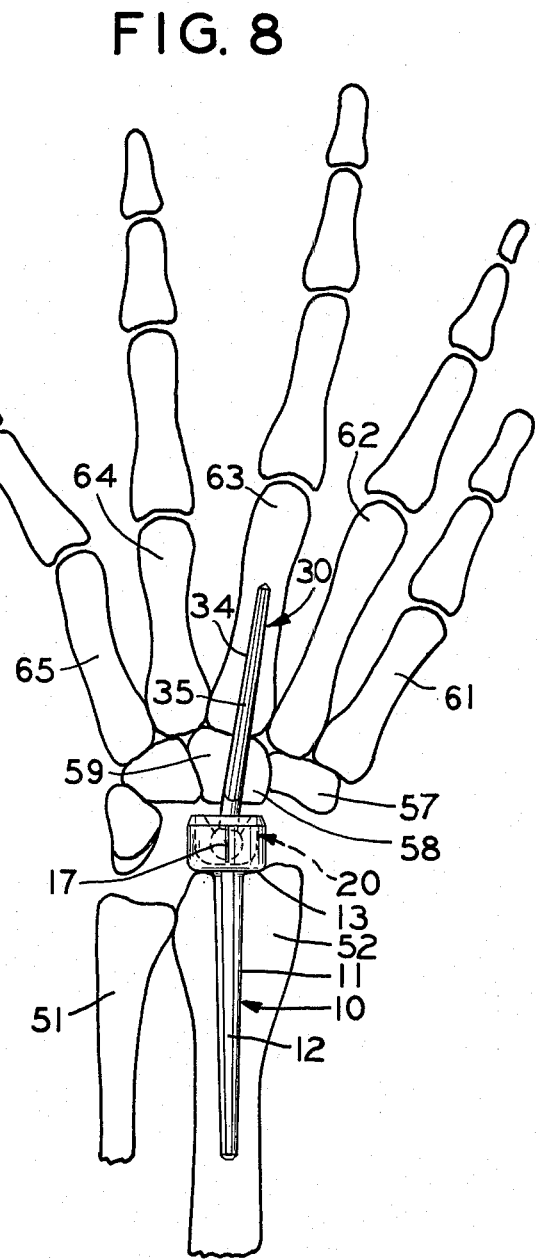
FIG. 8 shows a normal wrist with the prosthesis in place.

The normal wrist (FIG. 7) comprises three sets of bones: the forearm, the carpals and the metacarpal bones in the hand. The carpals are the bones most closely associated with the motion of the wrist. In the forearm there are two bones, the ulna 51 and the radius 52. In the hand there are eight carpals, which are divided into two rows, the proximal and the distal. The proximal row comprises a navicular 53, a lunate 54, a triquetrum 55 and a pisiform 56. The distal row comprises a trapezium 57, a trapezoid 58, a capitate 59 and a hamate 60. There are five metacarpals consecutively numbered 61–65 from the thumb through the last finger.

The bones are moved by soft tissue, tendons and ligaments. Of major importance for this present invention are the extensor tendons, flexor tendons, and the extensor retinaculum. The tendons provide extension and flexion respectively, and are located posterior to and anterior to the bones. Overlaying the extensor tendons is the extensor retinaculum, which holds down the extensor tendons and thereby prevents bowstringing.

To implant the prosthesis a dorsal approach is used, preserving the extensor retinaculum. The distal end of the radius 51 and the proximal ends of the carpals are exposed. The distal end of the radius is suitably resected to form a plane perpendicular to the volar plane. The lunate 54 and onehalf of the capitate 59 are removed. It may be necessary to remove a portion of the proximal end of the navicular 53, if it inhibits radial or ulnar deviation. The exposed medullary canal is reamed deep enough to contain the radial stem 11 and to have the proximal end of the cup 13 against the radius 52. The guide 12, and the groove 17 are beneficial for alignment of the radial component by defining its posterior surface.

The metacarpal component 30 is inserted into the intramedullary canal of the third metacarpal after suitable reaming and resection. The channel is deep enough to allow the metacarpal stem 34 to fit so that the distal surface of the step 33 abuts bone. The guide 35 on the metacarpal stem 34 serves the same function as the guide 12 on the radial stem 11, to insure proper alignment by defining the posterior surface of the component.

The components are assembled by the locking means. The concavo-convex component 20 is oriented so that the outer surface 25 is aligned with the pins 16. The member is then pushed into cup 13 until the convex surface 21 bottoms on the concave surface 14. The wrench is taken and its locking studs 44 are placed in the slots 28 on the frontal plane 29 of the member. A 90° rotation of the wrench rotates the concavo-convex member within the cup and around the ball 31 so that the pins 16 follow the slots 26 into the apertures 27 which holds them securely. The slots 26 become shallower toward the apertures 27 to prevent slippage of the member.

After the components are assembled, the wrist is moved through its range of motion to check the placement of the implant. Once the placement and range of motion are checked, the wrist is disassembled by unlocking the socket from the cup. The components are removed and the medullary canals are filled with a suitable bone cement. The components are replaced in the canals, aligned and assembled. Excess cement is collected in the notch 36 of the step 33 and proximal to the proximal surface of the cup 13. The collection of the cement by these surfaces increases the fixation of the implant.

In closing the incision, the extensor retinaculum is divided so that the distal half can be sutured over the implant and the proximal half can be sutured under the extensor tendons. The function of the division is to cover the implant, thereby preventing friction between the implant and the tendons. The division of the retinaculum also relocates the tendons and keeps them from lateral or medial slippage. Lastly, the division prevents bowstringing, just as the natural ligament does.

When the wrist is assembled and implanted, certain operational characteristics are apparent. Normally the ball 31 is free to rotate within the spherical surface 22. When the prosthesis is implanted such 360° rotation is impossible because the stem 34 is secured within the metacarpal. The possible motion which is allowed is circumduction as constrained by the articulation of the neck 32 within the frusto-conical surface 23 of the socket. The neck does not continually contact the frusto-conical surface, but is free to move within the opening defined by the frusto-conical surface. When it does contact the frusto-conical surface, there is an area of contact, as opposed to a line of contact. The area contact is due to the elliptical cross-section of the neck 32. If the neck had a circular cross-section then there would be line contact. The disadvantage of line contact is that it would increase the stress on the bearing surface. Maximum area of contact occurs for maximum loads at full dorsiflexion and palmar flexion. Minimum area of contact occurs during ulnar or radial deviation.

When viewed in a neutral position, the longitudinal axis of the metacarpal and radial components are coextensive. The center of rotation of the ball 31 is offset from the longitudinal axis in a volar direction (anterior direction). The offset gains mechanical advantage for the extensor tendons by granting them a sufficient moment arm. This is distinguished from prior wrist art in which the centers of rotation are not displaced volarward.

The wrench is distinguished by the connector 42. This connector allows for ease of placement and turning of the wrench during surgery. It was found that a straight line wrench was unwieldy in surgery.

While there have been described herein what at present are considered to be the preferred embodiments of the instant invention, it will be readily appreciated by those skilled in the art that various changes and modifications may be made in the practice of the instant invention without departing from its spirit and scope.

What is claimed is:

1. A wrist joint comprising:
   a. a first component having a tapered stem connected to a cup member, said cup being offset from the stem;
   b. a concavo-convex member adapted to fit within the cup and having concave and convex surfaces;
   c. a third member having a spherical ball surface which fits within the concavo-convex member;
   d. said third member having a tapered stem;
   e. means for locking said concavo-convex member within said cup to secure the prosthetic joint against substantial longitudinal pull;
   f. said first component being axially coextensive with the stem of the third member; and
   g. said concave surface of the concavo-convex member flaring outwardly to a frusto-conical surface which is elliptical in cross section.

2. The joint of claim 1 in which the connection between the spherical ball surface and the tapered stem is a neck having an elliptical cross-section which coacts with the frusto-conical surface to reduce the stress concentration between the neck and the concavo-convex member,
   and further in which the major axis of the elliptical neck is perpendicular to the major axis of the frusto-conical surface.

3. A wrist joint comprising:
   a. a first radial component having a tapered intramedullary stem;
   b. a cup fixedly connected thereto and offset to one side;
   c. a socket fitted within the cup and further having a spherical surface covering substantially more than a hemisphere;
   d. a metacarpal component having a ball, a neck portion and an intramedullary stem;
   e. said radial component and said metacarpal stem being coextensive;
   f. said ball fitted within said spherical surface of said socket, and further having an offset in the neck portion; and
   g. said socket having a frusto-conical surface extending outwardly from the spherical surface adapted to engage the neck of the metacarpal component to relieve the stress in the socket.

4. The joint of claim 3 in which the frusto-conical surface has an elliptical cross-section providing greater angular movement in dorsiflexion and palmar flexion and an acceptable angular movement in the ulnar and radial deviations.

* * * * *